US00PP12190P2

(12) United States Plant Patent
Evers

(10) Patent No.: US PP12,190 P2
(45) Date of Patent: Nov. 6, 2001

(54) ROSE PLANT NAMED 'TANORONEZ'

(75) Inventor: Hans-Jürgen Evers, Uetersen (DE)

(73) Assignee: Rosen Tantau Mathias Tantau, Nachfolger (DE)

( * ) Notice: Subject to any disclaimer, the term of this patent is extended or adjusted under 35 U.S.C. 154(b) by 0 days.

(21) Appl. No.: 09/438,183

(22) Filed: Nov. 11, 1999

(51) Int. Cl.[7] ..... A01H 5/00

(52) U.S. Cl. ..... Plt./108

(58) Field of Search ..... Plt./108, 102

*Primary Examiner*—Bruce R. Campell
*Assistant Examiner*—June Hwu
(74) *Attorney, Agent, or Firm*—Webb Ziesenheim Logsdon Orkin & Hanson, P.C.

(57) ABSTRACT

The new cultivar is a variety of rose plant having a compact growth habit. The plant exhibits a rich flowering habit, producing large, intensely red flowers. The plant also exhibits good disease resistance and is winter hardy.

1 Drawing Sheet

BACKGROUND OF THE NEW PLANT

The present invention includes a new and distinct rose plant known by the varietal name 'Tanoronez'.

The new plant was the result of a planned breeding program to produce a rose plant of the shrub/groundcover variety which is resistant to disease, and which has large, intensely red flowers. In the year 1993, the breeders crossed a "Tanotax" variety pink shrub rose (German Registration No. ROS 836) with a red groundcover rose plant of the Rosen Tantau Mathias Tantau Nachfolger private breeder's collections in Uetersen, Germany.

The new plant is distinguishable by its large, intensely red flowers, its rich flowering habit, its compact growth, its disease resistance and winter hardiness. The plant can be propagated asexually on *Rosa canina* rootstock or onto its own roots. It has been asexually reproduced in Schleswig-Holstein, Germany. Continued observations over a six year period from the vegetative cuttings in Uetersen, Germany, have confirmed that the distinguishing features of this new cultivar come true, remain stable and are retained through successive propagations.

DESCRIPTION OF THE DRAWING

The accompanying photographic drawing illustrates the new cultivar. Colors are described in reference to The Royal Horticultural Society (London) Colour Chart.

DESCRIPTION OF THE NEW PLANT

The following description sets forth the characteristics of the new cultivar. Observations were made on a 2 year old plant, propagated by budding into *Rose canina Intermis* root stock, and grown in an outdoor field in the area of Schleswig-Holstein, Germany.

The plant:
- *Botanical name.*—*Rosa L. domestica.*
- *Growth habit.*—Flat, bushy, closed and compact.

Size:
- *Height.*—60 cm.
- *Width.*—60 cm.

Habit: Flat, bushy, closed and compact.
Growth vigor: Strong.

Wood color: New—Green Group 141A; old—Greyed-Orange Group 174A.
Prickle:
- *Color.*—Young: Green Group 141A. Mature: Greyed-Orange Group 175B.
- *Size.*—Length: 0.5 cm. Width: 1.7 cm at stem.
- *Shape.*—Hooked downward.
- *Location on stem and branches.*—Around the stem.

Disease resistance: Very good as to downy mildew and black spot average as to powdery mildew and rust.
Hardiness: Very good to −10 degree C. winter killing in moderate climate zone.

FOLIAGE

Arrangement: Alternate.
Number of leaflets on typical stem leaves: 5.
Leaflets:
- *Size.*—Fully grown length: 6 cm. Fully grown width: 4 cm.
- *Color.*—Upper surface: Green Group 139A. Lower surface: Green Group 138B.
- *Shape.*—Pointed oval.
- *Texture.*—Leathery.
- *Margin.*—Serrulate.
- *Petiole.*—Color: Green Group 141C. Size: Length: 8 cm. Width: 0.2 cm.
- *Rachis.*— Color: Green Group 141A. Size: Length: 3 cm. Width: 1 cm.
- *Stipules.*—Size: Length: 2 cm. Width: 1 cm. Shape: Bearded. Color: Upper surface: Green Group 141B Lower surface: Green Group 141C.

BUD

Size:
- *Length.*—0.2 cm.
- *Width.*—0.3 cm.

Shape: Pointed ovoid.
Color: Red Group 46A.
Color changes during opening: None.
Sepals:
- *Size.*—Length: 2.1 cm. Width: 0.6 cm.
- *Color.*—Upper surface: Green Group 138C. Lower surface: Green Group 141A.

*Texture.*—Covered with some hairs on upper surface with no hair on lower surface.
*Shape.*—Oval.

Receptacle:
*Color.*—Green Group 137C.
*Shape.*—Funnel.
*Size.*—1 cm in diameter.
*Texture.*—Smooth.

Peduncle:
*Color.*—Green Group 141C with Greyed-Orange Group 172A when exposed to sunlight.
*Length.*—Approximately 3 cm.
*Strength.*—Stiff.
*Texture.*—No prickles.

FLOWER

Borne (number in clusters): 6–15.
Size (diameter): 6 cm in diameter.
Form: High-centered.

Petals:
*Number per flower.*—20–22.
*Color.*—Upper surface: Red Group 46A. Lower surface: Red Group 46B. Color changes with maturity: Tendency toward Red Group 53A. Base of petal: Green-White Group 157C.
*Texture.*—Soft.
*Size.*—Length: 4 cm. Width: 3 cm.
*Shape.*—Long oval with mucronate tip.
*Persistence.*—Petals drop off before drying.
*Lastingness.*—Approximately 5–7 days.

Fragrance: None.
Blooming period: Continuously.

REPRODUCTIVE ORGANS

Stamens:
*Number.*—Many.
*Anther.*— Length: 0.1 cm. Width: 0.05 cm. Color: Yellow-Orange Group 17A Pollen: Yellow-Orange Group 17A.
*Filament.*—Length: 2 cm. Width: 0.08 cm. Color: Yellow-Orange Group 16B. Pollen color: Yellow-Orange Group 17A.

Pistils:
*Length.*—4 cm.
*Number.*—8–10.
*Style.*—Color: Green Group 142D. Length: 1 cm. Width: 0.5 cm.
*Stigma.*—Color: Green Group 138D. Length: 2 cm. Width: 0.08 cm.
*Hips.*—None produced.

I claim:

1. A new and distinct variety of rose plant substantially as shown and described.

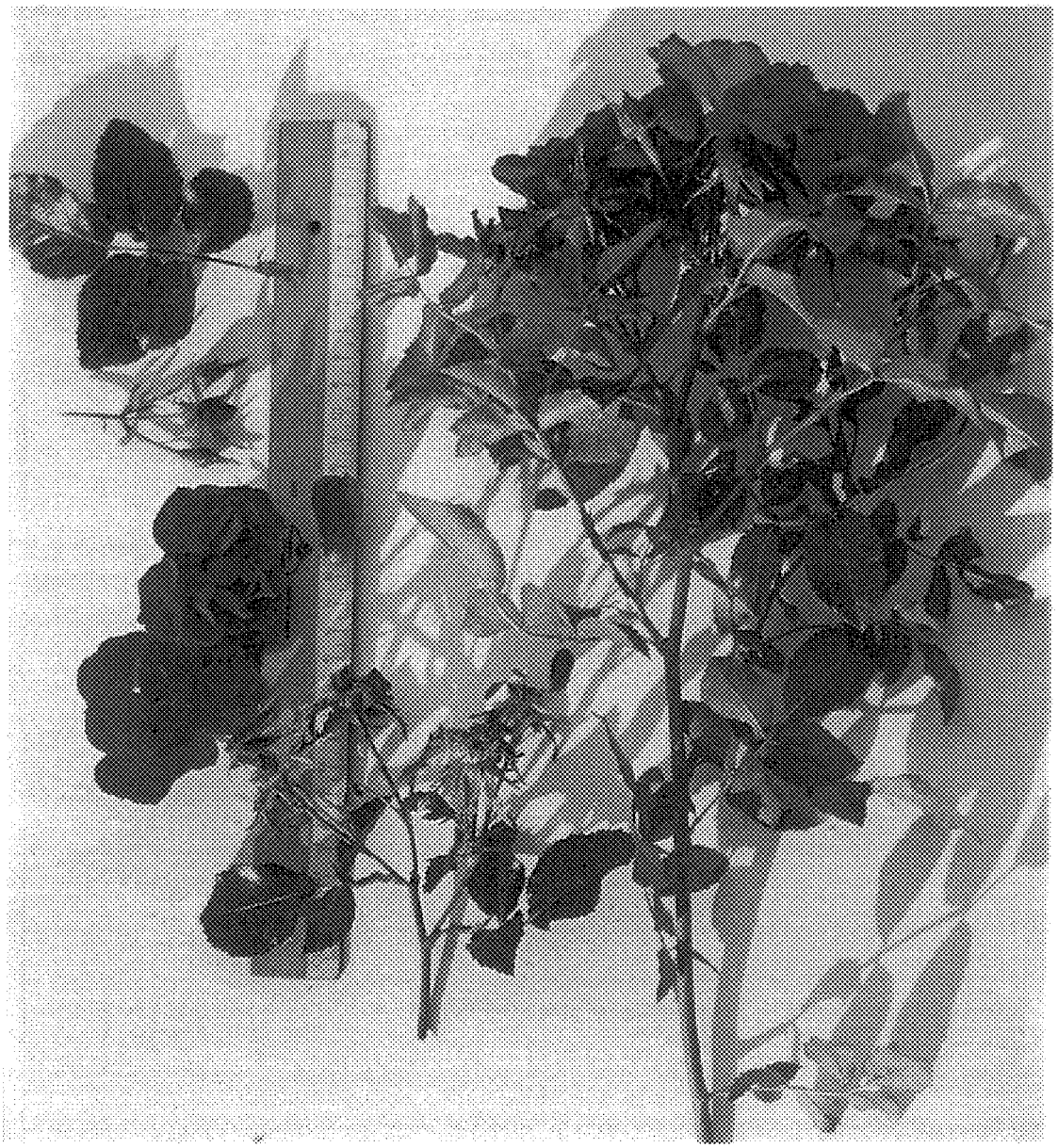

* * * * *